United States Patent [19]

Ort

[11] Patent Number: 4,652,445
[45] Date of Patent: Mar. 24, 1987

[54] HAIR TREATMENT AND CONDITIONER

[76] Inventor: Philip Ort, 1386 E. 21st St., Brooklyn, N.Y. 11210

[21] Appl. No.: 760,896

[22] Filed: Jul. 31, 1985

[51] Int. Cl.⁴ .......................... A45D 7/00; A61K 7/06
[52] U.S. Cl. .......................................... 424/70; 132/7; 514/494
[58] Field of Search ............... 424/70; 514/494; 132/7

[56] References Cited

U.S. PATENT DOCUMENTS

| 4,053,630 | 10/1977 | Yu et al. | 514/494 |
| 4,146,636 | 3/1979 | Soler | 514/494 |
| 4,161,526 | 7/1979 | Gorman | 514/494 |
| 4,214,000 | 7/1980 | Papa | 514/494 |

FOREIGN PATENT DOCUMENTS

| 0038246 | 10/1981 | European Pat. Off. | 514/494 |
| 0074819 | 3/1983 | European Pat. Off. | 424/70 |
| 2128148 | 3/1971 | France | 514/494 |
| 2338248 | 1/1976 | France | 514/494 |
| 2293924 | 7/1976 | France | 514/494 |
| 0112906 | 9/1979 | Japan | 514/494 |
| 54-15913 | 11/1979 | Japan | 514/494 |
| 0029900 | 2/1983 | Japan | 424/70 |
| 2109685 | 6/1983 | United Kingdom | 514/494 |

Primary Examiner—Dale R. Ore
Attorney, Agent, or Firm—Goodman & Teitelbaum

[57] ABSTRACT

A hair conditioner product including conditioner ingredients with the addition of zinc releasing ingredients for providing available zinc molecules for binding to the amino acids within each hair shaft for improved hair quality. The zinc releasing ingredients include a zinc amino acid complex, and preferably a zinc gluconate.

23 Claims, No Drawings

HAIR TREATMENT AND CONDITIONER

BACKGROUND OF THE INVENTION

This invention relates to hair treatment, and more particularly to a novel hair conditioning product for improved hair quality, and a new method of treating the hair to provide improved hair quality.

In the treatment of hair, normally a shampoo or medicated soap is applied for the actual cleaning of the hair. However, such shampoos or soaps typically leave the hair knotty, difficulty to manage, and stiff. In order to improve the hair quality, it is well known to apply hair conditioners subsequent to the shampoo treatment. The hair conditoners are generally applied while the hair is still wet as the final cycle in the cleaning of the hair. The hair conditioner is applied either as part of the shampoo, or as an additional solution subsequent to the shampoo. The hair conditioner is rubbed into the hair, following which it is rinsed out of the hair. The final rinsing of the hair removes all excess chemicals.

Typical hair conditioners have been found quite useful for eliminating the knots and stiffness of the hair, whereby the hair becomes more manageable. However, continued use of such hair conditioners tends to make the hair too soft, limp and lifeless, with no body to hold the shape thereof. Also, the known hair conditioners usually leave the hair greasy as a result of continued buildup of wax and oil resulting from the hair conditioner ingredients. In this manner, the natural shine of the hair is lost.

There is therefore needed a hair conditioner which will provide the manageability quality needed following the normal shampoo of the hair, but at the same time does not soften the hair appreciably to make it limp, does not cause a greasy buildup, and does not cause a loss of its shine.

SUMMARY OF THE INVENTION

Accordingly, an object of the present invention is to provide a new hair conditioner which avoids the prior art problems of existing hair conditioners.

Another object of the present invention is to provide a hair conditioner which prevents knotting of the hair and makes the hair manageable, and at the same time strengthens the hair without leaving any residue or wax buildup in the hair.

A further object of the present invention is to provide a hair conditioner which increases the body and bounce of the hair, while retaining hair strength.

Still a further object of the present invention is to provide a hair conditioner which will supply the hair with a natural zinc level to prevent a zinc deficiency which can result from normal shampooing of the hair.

Yet a further object of the present invention is to provide a hair conditioner which can be used to maintain a balanced zinc level within the hair, thereby creating a healthy molecular structure for the hair with full body and improved elasticity.

A further object of the present invention is to provide a hair conditioner which can be utilized for all types of hair conditions.

Another object of the present invention is to provide an improved method of treating the hair by application of a hair conditioner onto the hair after shampooing of the hair, whereby no rinsing out of the hair conditioner is needed.

Briefly, in accordance with the present invention, there is provided a hair conditioner product which includes hair conditioning chemicals, with the addition of zinc releasing chemicals which provide available zinc molecules for binding to the amino acids within the hair shaft, for improved hair quality.

In an embodiment of the invention, the zinc releasing chemicals include a zinc amino acid complex, and can further include zinc gluconate. Monohydric, dihydric, or polyhydric acids such as citric acid or acetic acid can also be added for maximum utilization of the zinc so that the zinc can react better with the hair.

Further ingredients can be added such as opacifiers, fragrances, and dyes as needed, and also, a pro-vitamin can be included to make the hair more manageable and make the solution absorbed on the surface of the hair.

The aforementioned objects, features and advantages of the present invention will, in part, be pointed out with particularity, and will, in part become obvious from the following more detailed description of the present invention.

DESCRIPTION OF THE PREFERRED EMBODIMENT

The present invention provides for an improved hair conditioner which utilizes zinc releasing ingredients for providing zinc molecules that can bind to the amino acids within the hair shaft for improved hair quality. The zinc in the hair frequently gets washed out during normal shampooing. Also, through over processing or even from dietary habits, a zinc deficiency in the hair can occur.

The presence of an appropriate zinc level creates healthy molecular structure with full body and improved elasticity of the hair. Normal hair conditioners are useful in providing the manageability of the hair. However, they also tend to cause softening of the hair with an accompanying loss of body and structure.

The prior art hair conditioners further tend to leave a waxy finish on the hair as a result of the wax and oil present in the hair conditioners. Furthermore, the natural shine of the hair is likewise lost with the prior art hair conditioners.

By the addition of the zinc releasing ingredients, zinc molecules are available for forming a bond on the helix bridge between the cysteine molecules in the hair strands. This is similar to the sulfur bridges already existing in the hair. By means of the addition of the zinc which combines with the hair, the hair is strengthened and there is created a healthy molecular structure with full body and improved elasticity to the hair.

The zinc releasing ingredients that can be added to the hair conditioner, are typically a zinc amino acid complex. More specifically, a zinc protein complex can be utilized, and even more specifically, a zinc keratin complex can be utilized.

Zinc gluconate or other zinc salts may be added to the zinc amino acid complex solution in order to enhance the zinc utilized by the hair shaft.

The typical hair conditioners that are utilized in the present product are fatty quaternium chlorides. More specifically, stearalkonium chloride is utilized which conditions the hair and makes it manageable. Also, as part of the hair conditioners, quaternium-7 can be utilized, which also provides for the conditioning of the hair by using a lesser quantity thereof, thereby lessening the softening effect of the conditioning ingredients.

The normal pH of the zinc amino acid complex is pH 1.5–5.0. The normal pH of the zinc gluconate is pH 1.5–4.0. In order to bring down the pH level of the solution, various acids can be included. By way of example, there can be included monohydric acid such as acetic acid, trihydric acid such as citric acid, or other dihydric or polyhydric acids could also be utilized. Such acids also serve to improve the reaction of the zinc with the hair so as to maximize utilization of the zinc.

The present product can also include pro-vitamins. These are one of the ingredients that the body uses to make vitamins. By the addition of such pro-vitamins to the present product, it permits the hair to become even more manageable, makes the hair soft and silky. Also, by use of the pro-vitamin, the present product becomes better absorbed on the surface of the hair. One typical pro-vitamin which can be utilized is DL panthenol.

Other additions to the product can include opacifiers, which are added to make a clear solution opaque, and give the solution body and substance. Usual opacifiers which can be added are mica and titanium dioxide. These are generally added more for cosmetic reasons than of necessity for the improvement of hair quality. An alternate opacifier which can be utilized is bismuth oxychloride.

In order to complete the product, various fragrances may be added in order to provide a desired scent. Also, various types of dyes can be added, as is necessary for a desired color. By way of example, in a particular product, D & C Red No. 6 dye was added, such being a commercially available dye.

In order to complete the product, water is added as required to complete 100% of the solution.

In a typical product which has been provided and tested, the contents were as follows:

|  | RANGE | PREFERRED |
| --- | --- | --- |
| STEARALKONIUM CHLORIDE | 0.1–5.0% | 0.5–3.0% |
| QUATERNIUM-7 | 0.05–3.0% | 0.1–2.5% |
| DL PANTHENOL | 0.05–5.0% | 1.0–2.0% |
| ZINC AMINO ACID COMPLEX (Zinc Protein Complex) | 0.05–5.0% | 0.5–2.0% |
| ZINC GLUCONATE | 0.05–5.0% | 0.5–3.0% |
| MICA | 0.1–1.0% | 0.2–0.8% |
| TITANIUM DIOXIDE | 0.05–2.0% | 0.2–1.0% |
| CITRIC ACID (Acetic Acid) | .05–7.5 | 0.3–2.0 |
| FRAGRANCE - as necessary for desired scent. | | |
| D & C RED NO. 6 (dye) - as necessary for desired color. | | |
| WATER - as required to complete 100% of solution. | | |

In the above example, the range indicates the approximate amounts of each of the items that should be included in the solution. However, the preferred amounts are indicated for a preferred product.

If bismuth oxychloride is utilized in place of the mica and titanium dioxide, the range of the bismuth oxychloride to be utilized is 0.01–5.0% with a preferred range of 0.05–1.0%.

In applying the present product, the hair should be first shampooed and then lightly towel dried. An appropriate amount of the present product is then applied to the hair and is massaged into the hair. The hair is then combed through for complete coverage. No rinsing should be done after application of the present product.

The present product can be used on all types of hair with the amount of the product varying depending upon the hair condition. By way of example, for a hair condition of fine-thin or oily-limp, one unit of the present product should be applied. For a hair condition of dry-dull or coarse-brittle, two units should be applied. For over-processed hair or heat or sun damaged hair, three units should be applied. The present product can also be used as a regular zinc level maintenance of the hair with one unit being applied. Typically, a unit is approximately 1.0 oz.

The present product was tried and tested on numerous individuals having all types of quality of hair, density of hair, and hair lengths.

The condition of the hair of the users varied from dry, fine, limp, and dull. The product was tried on all types of hair problems including split hair, brittle hair, porous and snarled hair, and was even utilized for hair that was overprocessed, over-bleached, or severly damaged. In each case, after treatment, the comb-out of the hair was found to be very easy and the hair was found to be easy to manage. The texture was full body and bouncy, and there was a luster and sheen to the hair. In no case was there any unfavorable reaction to the product, and in no case was there any negative after-effect even after continued usage.

There has been disclosed heretofore the best embodiment that the invention presently contemplated. However, it is to be understood that various changes and modifications may be made thereto without departing from the spirit of the present invention.

What is claimed is:

1. In a hair conditioner product containing a solution including conditioning ingredients for making the hair manageable, wherein the improvement comprises the addition of:
    a zinc releasing chemical to said solution for providing zinc molecules for binding to amino acids contained within each hair shaft for strengthening the hair and to provide a healthy molecular structure with full body and improved elasticity to the hair;
    said zinc releasing chemical selected from the group consisting of a zinc protein complex, a zinc keratin complex and a zinc amino acid complex; and
    said zinc releasing chemical being in the range of 0.05–5.0% of said solution.

2. A hair conditioner product as in claim 1, wherein said zinc releasing chemical comprises a zinc protein complex.

3. A hair conditioner product as in claim 2, wherein said zinc protein complex is a zinc keratin complex in the range of 0.5–2.0% of said solution.

4. A hair conditioner product as in claim 1, wherein said zinc releasing chemical further includes a zinc gluconate in the range of 0.05–5.0% of said solution to provide additional zinc for coacting with said zinc releasing chemical to enhance the zinc utilized by the hair shafts.

5. A hair conditioner product as in claim 1, and further comprising at least one of a monohydric acid, a dihydric acid, or a polyhydric acid in the range of 0.05–7.5% of said solution to reduce pH level of said solution.

6. A hair conditioner product as in claim 1, and further comprising citric acid in the range of 0.05–7.5% of said solution for improving the binding action of the zinc molecules within the hair shafts.

7. A hair conditioner product as in claim 1, and further comprisng acetic acid in the range of 0.05–7.5% of said solution for improving the binding action of the zinc molecules within the hair shafts.

8. A hair conditioner product as in claim 1, wherein said conditioning ingredients include a fatty quaternium chloride, said fatty quaternium chloride comprising stearalkonium chloride in the range of 0.1–5% of said solution and quaternium-7 in the range of 0.05–3.0% of said solution.

9. A hair conditioner product as in claim 1, and further comprising a pro-vitamin in the range of 0.05–5.0% of said solution to further improve hair quality.

10. A hair conditioner product as in claim 9, wherein said pro-vitamin comprises DL panthenol.

11. A hair conditioner product as in claim 1, and further comprising a fragrance and a dye, as required.

12. A hair conditioner product as in claim 1, and further comprising an opacifier in the range of 0.05–3.0% of said solution for controlling clarity of resulting product.

13. A hair conditioner product as in claim 12, wherein said opacifier comprises bismuth oxychloride.

14. A hair conditioner product as in claim 12, wherein said opacifier comprises mica in the range of 0.1–1.0% of said solution and titanium dioxide in the range of 0.05–2.0% of said solution.

15. A hair conditioner solution comprising:
conditioning ingredients for making the hair manageable comprising stearalkonium chloride in the range of 0.1–5.0% and quaternium-7 in the range of 0.05%–3.0%;
a pro-vitamin to further improve hair quality comprising DL panthenol in the range selected from the group consisting of a zinc protein complex, a zinc keratin complex and a zinc amino acid complex of 0.05–5.0%;
zinc releasing chemical for providing zinc molecules for binding to amino acids contained within each hair shaft for strengthening the hair and to provide a healthy molecular structure with full body and improved elasticity to the hair in the range of 0.05–5.0%, and further comprising zinc gluconate in the range of 0.05–5.0% to provide additional zinc for coacting with said zinc releasing chemical to enhance the zinc utilized by the hair shafts;
citric acid in the range of 0.05–7.5% for improving the binding action of the zinc molecules within the hair shafts; and 16. A hair conditioner solution as in claim 15, wherein said zinc releasing chemical has a pH of between 1.5 and 5.0, and said zinc gluconate has a pH of between 1.5–4.0.

17. A hair conditioner solution as in claim 15, further including an opacifier for controlling clarity of said solution comprising mica in the range of 0.1–1.0%, and titanium dioxide in the range of 0.05–2.0%.

18. A hair conditioner solution as in claim 17, and further comprising a fragrance and a dye, as required.

19. A hair conditioner solution as in claim 15, and further including an opacifier for controlling clarity of said solution comprising bismuth oxychloride in the range of 0.01–5.0%.

20. A hair conditioner solution as in claim 17, wherein
said stearalkonium chloride is in the range of 0.5–3.0%;
said quaternium-7 is in the range of 0.1–2.5%;
said DL panthenol is in the range of 1.0–2.0%;
said zinc amino acid complex is in the range of 0.5–2.0%;
said zinc gluconate is in the range of 0.5–3.0%;
said mica is in the range of 0.2–0.8%;
said titanium dioxide is in the range of 0.2–1.0%; and
said citric acid is in the range of 0.3–2.0%.

21. A method of treating hair comprising the steps of:
shampooing the hair;
applying a hair conditioner solution comprising zinc releasing means for providing zinc molecules for binding to amino acids contained within each hair shaft for strengthening the hair and to provide a healthy molecular structure with full body and improved elasticity to the hair, said zinc releasing chemical selected from the group consisting of a zinc protein complex, a zinc keratin complex and a zinc amino acid complex in the range of 0.05–5.0% of said hair conditioner solution; and
leaving the hair conditioner solution in the hair without rinsing.

22. A method of treating hair as in claim 21, wherein said zinc amino acid complex is zinc keratin complex.

23. A method of treating hair as in claim 21, wherein said zinc releasing chemical further includes a zinc gluconate in the range of 0.05–5.0% of said solution to provide additional zinc for coacting with said zinc amino acid complex to enhance the zinc utilized by the hair shafts.

* * * * *